United States Patent [19]

Toyomizu et al.

[11] Patent Number: 5,725,894

[45] Date of Patent: Mar. 10, 1998

[54] COCCIDIOSIS-RELIEVING AGENT AND FEED CONTAINING THE SAME

[75] Inventors: Masaaki Toyomizu; Yutaka Nakai, both of Miyagi, Japan

[73] Assignee: Takasago International Corporation, Tokyo, Japan

[21] Appl. No.: 605,739

[22] Filed: Feb. 22, 1996

[30] Foreign Application Priority Data

Feb. 23, 1995 [JP] Japan .................................... 7-058278

[51] Int. Cl.$^6$ .............................. A23K 1/16; A23K 1/18; A61K 35/78; A61K 31/60

[52] U.S. Cl. .............................. 426/2; 426/629; 426/630; 426/632; 426/655; 426/417; 426/425; 426/429; 426/807; 514/570

[58] Field of Search ................................ 426/2, 629, 630, 426/632, 655, 417, 425, 429, 807; 514/570

[56] References Cited

U.S. PATENT DOCUMENTS 5,240,962  8/1993  Nakatsu et al. .................... 514/570

OTHER PUBLICATIONS

Kubo et al, Molluscicides from the Cashew *Anacardium occidentale* and Their Large–Scale Isolation, 1986, 970–973 (vol. 34, No. 6).

*Primary Examiner*—David L. Lacey
*Assistant Examiner*—Choon Koh
*Attorney, Agent, or Firm*—Sughrue, Mion, Zinn, Macpeak & Seas, PLLC

[57] ABSTRACT

A coccidiosis-relieving agent comprising cashew nut shell oil and/or anacardic acids as an active ingredient and a feed for relieving coccidiosis comprising cashew nut shell oil and/or anacardic acids. Cecal lesions of livestock and poultry, in particular poultry such as fowl, can be relieved by adding cashew nut shell oil and/or anacardic acids to a feed. The coccidiosis-relieving agent according to the present invention does not completely inactivate Coccidium protozoa, but induces slight infection to immunize an animal, thus achieving a so-called "passive immunological effect". The coccidiosis-relieving agent is efficacious in allowing Coccidium protozoa to grow and imparting sufficient immunological stimuli while relieving lesions to thereby lessen damage to poultry such as fowls.

12 Claims, No Drawings

COCCIDIOSIS-RELIEVING AGENT AND FEED CONTAINING THE SAME

FIELD OF THE INVENTION

This invention relates to a coccidiosis-relieving agent and a feed containing the same. More particularly, it relates to a coccidiosis-relieving agent containing cashew nut shell oil and/or anacardic acids as an active ingredient and a feed containing the same.

BACKGROUND OF THE INVENTION

It is known that the pathogenicity of coccidiosis, which is an infectious disease observed in various animals including livestock and poultry, lies in protozoa belonging to EIMERIORINA (the true coccidia) of the Protozoa.

However, coccidiosis in livestock (cow, sheep, goat, rabbit, etc.), poultry (fowl, turkey, quail, etc.) and pets (dog, cat, etc.) are mostly caused by infection with protozoa belonging to the genus Eimeria or Isospora.

As the pathogens of avian coccidiosis, there have been identified 9 protozoa belonging to the genus Eimeria, namely, *E. tenella, E. necatrix, E. maxima, E. acervurina, E. brunetti, E. mivati, E. mitis, E. praecox* and *E. hagani*.

With the recent prosperity of poultry farming and the enlargement of the feeding scale, there has been a great increase in the influences of avian coccidiosis.

Each of protozoa belonging to the genus Eimeria, which are the pathogens of avian coccidiosis, has a high host specificity and is parasitic on a highly restricted site in the intestinal tract. These protozoa differ in pathogenicity from each other. Among all, *E. tenella* shows the strongest pathogenicity and causes the largest damage to poultry farming. It is parasitic on the cecum of a fowl and destroys the intestinal wall. As a result, the host bird suffers from hemorrhage and has blood in its stool, followed by death in many cases. That is, poultry farming is badly damaged thereby.

There have been developed various drugs as coccidiostats. First, sulfa drugs were proposed as drugs for treating arian coccidiosis. Owing to its potent efficacy, in particular, it was recommended to use sulfaquinoxaline around 1947. Subsequently, however, the protozoa acquired resistance to this drug and thus it was used in the form of blends with other drugs. Then attempts were made to reduce the dose or enhance the efficacy by combining these drugs with folic acid antagonists to achieve synergistic effects. For example, it was reported that a mixture of sulfamonomethoxine with ormetoprim (3:1) was efficacious when administered in a dose ⅕ times as much as sulfamonomethoxine alone [Animal Science and Technology (Journal of Japanese Society of Zootechnical Science), 6, 523 (1988)]. On the other hand, although nicarbazin, which is a molecular compound of dinitrophenylurea with dimethyl pyrimidinol developed in 1955, is efficacious in preventing arian coccidiosis, its administration is restricted to chicks aged 60 days or younger in order to minimize its influences on egg laying, etc.

Protozoa of the genus Eimeria require vitamin $B_1$ (thiamine) for their growth. Therefore, amprolium, which is one of vitamin $B_1$ antagonists (anti-thiamine compounds), has been mainly used for a long period of time as a drug for preventing avian coccidiosis with little side effect. In recent years, however, the efficacy of amprolium has been also deteriorated due to the acquisition of resistance, etc.

Under these circumstances, a polyether-series antibiotic called "monensin" was reported for the first time in 1967 as an efficacious antibiotic. Monensin serves as an ionophore which incorporates a metal ion (for example, alkali metal ion, alkaline earth metal ion) thereinto and makes it lipophilic. Since the effects of the existing drugs for preventing coccidiosis had been deteriorated, monensin rapidly increased its share in the market. However, monensin was subsequently replaced by salinomycin, which was another polyether-series antibiotic, because of efficacy and economical performance.

Since the protozoa also acquired resistances to these antibiotics, attempts have been made to solve this problem by combining meticlorpindol, which has been known as an active agent against avian coccidiosis, with lasalocid A which is a polyether-series antibiotic (JP-A-63-196515; the term "JP-A" as used herein means an "unexamined published Japanese patent application") and by inhibiting the growth of Coccidium protozoa by using a product obtained by an aldol addition reaction between 3-indoleacetaldehyde and p-hydroxyphenylacetaldehyde (JP-A-5-39265). Also, there have been developed novel drugs such as naphthyrinomycin A (JP-A-6-172111).

On the other hand, examples of synthetic chemicals usable as a drug for treating arian coccidiosis include clazuril which is a triazine compound. There has been reported a water soluble preparation containing this compound which is to be given together with water (JP-A-1-133430). Furthermore, there have been recently developed 1,2,3-triazinediones (JP-A-5-117250).

These compounds can exhibit preventive effects when added to a feed even in a small amount, i.e., 1 to 5 ppm. It has been also reported that therapeutic effects can be obtained by increasing the addition level. Although it has been energetically attempted to apply vaccines, no practical use has been established so far [Avian Diseases, 36, 1034 (1992); 37, 1113 (1993); J. Protozool Res., 4, 1 (1994)]. In addition, studies have been made on the application of monoclonal antibodies to diagnostic methods and the development of vaccines by biotechnology (JP-A-61-69798). Furthermore, attempts have been made to use drugs by turns so as to cleverly prevent the acquisition of resistance. Namely, it has been attempted to feed a fowl while changing drugs with its growth. However, there has been established hitherto neither the best or the most reliable drug nor any preventive or therapeutic method using the same.

As described above, protozoa of the genus Eimeria are highly specific to the host. Thus, a protozoan parasitic on fowls would not be parasitic on any other birds or animals. Protozoa of the genus Eimeria essentially have the same life cycle regardless of species. In the case of fowls, when a matured oocyst is incorporated into the bird body from outside, the oocyst wall is broken in the gizzard and thus 4 sporocysts are liberated. These sporocysts are transported into the intestine and 2 sporozoites are released from each sporocyst due to enzymatic actions. These sporozoites immediately invade into mucosal cells of the intestine followed by repeated division. Thus, schizonts each involving several to several hundred merozoites are formed within one to two days. After breaking the schizont membrane, the merozoites are liberated outside of the cells and invade into the mucosal cells again. Although some of the merozoites undergo repeated asexual reproduction (schizogony or merogony), most of them undergo sexual reproduction (gametogony) so as to give microgamates (male) and macrogamates (female). After the conjugation of these microgamates and macrogamates, fertilization is completed and the oocysts thus formed are released from the intestinal mucosa into the stool and then discharged.

Although the oocysts discharged from the bird body are immature ones having no infectivity, they mature and get infectious within several days in the presence of appropriate moisture and oxygen at an adequate temperature. After repeating this process, the infectivity is enhanced. It is observed that infection with 10,000 or more oocysts per animal causes death.

As described above, the problem of arian coccidiosis still remains unsolved in Japan, though there have been developed a number of drugs. This is because: (1) no effective method has been established for completely sterilizing oocysts of the protozoa causing coccidiosis; (2) the oocysts are very small in size (about 0.02 mm); (3) the oocysts have a high reproducibility (more than 10,000 ones per individual); (4) fowls are fed on the infectious source; (5) the immunity lasts only a short period of time in chickens (light infection: several weeks, serious infection: several months); (6) a preventive drug is used in a low dose by taking side effects into consideration, which causes the problem of the acquisition of resistance to the drug; and (7) it is hot and humid in summer in Japan.

It is appropriate to sterilize oocysts only when they exist outside the bird body. During this period, a relatively potent drug can be used. However, it is regrettable that no practically usable means for completely exterminating oocysts by using a drug has been established so far.

Although ammonia has the strongest sterilizing effect, it should be used at a concentration of at least 10% in order to achieve a satisfactory effect. Methyl bromide, which is a gas having a high sterilizing effect, is toxic. A mixture of o-dichlorobenzene and quinomethionate has potent effects, but it cannot achieve complete extermination.

On the other hand, heating may be cited as a physical means for sterilizing the oocysts. Namely, oocysts can be completely exterminated by heating at 60° C. for 1 hour, at 70° C. for 15 minutes, at 80° C. for 3 minutes or at 100° C. for several seconds. However, it is impossible in practice to heat all over a poultry house. Even though a steam cleaner, etc., is used, some parts of the poultry house remain unheated, which makes it difficult to completely exterminate oocysts.

To exterminate protozoa of the genus Eimeria, it has been the practice to continuously add a drug for preventive coccidiosis to a poultry feed. In this case, the parasites are killed when they enter the digestive tract of a fowl and liberate sporozoites into the intestinal tract. In an ideal case, the drug employed is not absorbed via the intestinal wall and thus it does not cause a problem of remaining drug in the chicken meat. However, no such a drug has been developed so far.

SUMMARY OF THE INVENTION

An object of the present invention is to provide a drug which can effectively solve the above-mentioned problems.

The present inventors have found out that cashew nut shell oil (hereinafter sometimes referred to simply as "CO") and/or its main component, anacardic acids (4-hydroxy-6-alkylbenzoic acid, hereinafter sometimes referred to simply as "AA") have an uncoupling effect on oxidative phosphorylation of hepatic mitochondria. They have also found through experiments using artificial liposomes that lipid-solution AA may act as an (−)-carrier, thus exerting a passive effect of relieving cecal lesions, though it does not affect the growth of the protozoa. The present invention has been completed based on these findings.

As described above, a polyether-series antibiotic is a substance which falls into the category of ionophore compounds having a carbonyl group in its molecule. It forms salts together with alkaline earth metals (sodium, potassium, magnesium, etc.). The metal ion of such a salt, which has been incorporated into the polyether molecule, shows no ionic properties but a high solubility in fat. Therefore, a metal ion (for example, sodium ion) passes through cells with the assistance of the polyether-series antibiotic and thus affects ion potential function of cell wall. It is considered that CO and AA may have functions similar thereto.

The present invention relates to a coccidiosis-relieving agent comprising cashew nut shell oil and/or anacardic acids as an active ingredient and a feed for relieving coccidiosis characterized by containing cashew nut shell oil and/or anacardic acids.

DETAILED DESCRIPTION OF THE INVENTION

The CO to be used in the present invention is a liquid oil contained in nut shells of cashew nut tree (*Anacardium occidentale L.*). CO can be obtained by solvent-extraction or heating. As a heating method, dry distillation has been generally employed. A common method for thermal dry distillation comprises heating unshelled cashew nuts to separate shells from nuts, heating the shells, optionally together with a small amount of CO, and separating the oil from the solid matters to give CO.

On the other hand, the solvent-extraction method is generally performed in the following manner. Nuts are separated from shells without heating. Then the shells are ground and extracted with a solvent followed by the elimination of the solvent. Examples of the solvent usable in this method include organic solvents, e.g., hydrocarbons such as n-pentane, n-hexane, n-heptane, n-octane, cyclohexane, cyclooctane, benzene, toluene and xylene, ketones such as acetone and methyl ethyl ketone, alcohols such as methanol and ethanol, esters such as methyl acetate and ethyl acetate. Among these solvents, n-hexane is frequently employed, since it is less expensive and can be easily obtained.

The cashew nut shell oil contains (1) cardanol, (2) cardol, (3) methylcardol and (4) anacardic acids. Anacardic acids are most preferable among these components for relieving coccidiosis. These components can be isolated in accordance with the known method as described in Isao Kubo et al., J. Agric. Food. Chem., 34, 970–973, 1986. In the shell oil obtained by the heating method, anacardic acids have been decarboxylated into cardanol and thus cardanol and cardol are contained as the main components. On the other hand, the shell oil obtained by the solvent-extraction method contains anacardic acids and cardol as the main components. To use anacardic acids, it is therefore preferable to employ the solvent-extraction method. Anacardic acids are usually contained in the shell oil in an amount of about 40% by weight.

Anacardic acids are represented by the following formula (I).

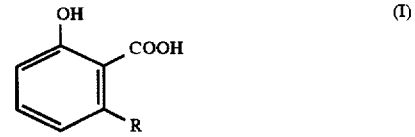

wherein R represents $C_{15}H_{25}$, $C_{15}H_{27}$, $C_{15}H_{29}$ or $C_{15}H_{31}$.

The above-mentioned substances can be isolated from cashew nut shell oil by a conventional purification means. For example, they may be eluted by silica gel column chromatography with the use of a solvent mixture of n-hexane, ethyl acetate and acetic acid while varying the mixing ratio (JP-A-3-240721, JP-A-3-240716).

In the present invention, cashew nut shell oil obtained by the extraction method or the heating method as described above and anacardic acids isolated from this shell oil can be used. A commercially available cashew nut shell oil (generally called "cashew nut oil") can also be used. Either one of these materials or a combination thereof may be used.

The coccidiosis-relieving agent of the present invention comprising cashew nut shell oil and/or anacardic acids as an active ingredient is orally administered to livestock or poultry in order to relieve coccidiosis. Administration of this coccidiosis-relieving agent to livestock or poultry can be made by methods commonly employed for a number of coccidiostats. For example, it may be added to a livestock or poultry feed. The coccidiosis-relieving agent may be administered either alone or in the form of a combination with other coccidiostats such as a sulfa drug or a folic acid antagonist. The dose of the coccidiosis-relieving agent practically administered widely varies from case to case depending on the type of the Coccidium to be exterminated and the severity of the infection.

The lower limit is the dose whereby coccidiosis can be relieved, while the upper limit is the dose whereby the suppressing or relieving effect cannot be improved any more.

The active components are diluted $10^2$ to $10^4$-fold when they are given to livestock or poultry. The coccidiosis-relieving agent may be given to livestock or poultry during a whole feeding period after their birth by allowing them to freely take a feed. Preferably, it can be given during a period when other drugs are not given in order to minimize the total doses of the drugs.

Cashew nut shell oil and/or anacardic acids (hereinafter referred to as the active component) can be added to a feed, for example, in the following manner. The active component is added to the feed typically in an amount of from 0.01 to 5.0% by weight, preferably from 0.1 to 1.0% by weight. It has been found out that such an amount of the active component significantly relieves the cecal contraction of a fowl suffering from coccidiosis.

As a matter of course, the content (i.e., concentration) of the active component in the composition (blend) to be given to livestock or poultry, in particular, fowls, varies depending on the type of the composition employed. One skilled in the art can easily determine an amount of the active component contained in the composition for relieving coccidiosis. In the most convenient case, the active component is used in the form of a powder and dissolved or dispersed in an acceptable solvent. Then it is added, as a component of a coccidiosis-relieving agent, to a feed composition. The active component may be added to a livestock or poultry feed in the form of a finely ground matter. Alternatively, it may be mixed with a carrier acceptable for oral administration to animals such as feed additives to give a premix for preparing the final product (i.e., a feed to be given to livestock or poultry) followed by the mechanical mixing with the final product. A livestock or poultry feed typically comprises molasses, fermentation residues, corn mill, ground or rolled oats, wheat short and coarse wheat flour, soybean cake, alfalfa, clover, meat pieces, born mill, mineral additives such as calcium carbonate, vitamins, etc.

According to the present invention, cecal lesions of livestock and poultry, in particular, poultry such as fowl, can be relieved by adding cashew nut shell oil and/or anacardic acids to a feed. The coccidiosis-relieving agent of the present invention can satisfy the poultry farmers' requirement for a so-called "passive immunological effect", namely, not completely exterminating Coccidium protozoa with a drug but immunizing fowls via slight infection. In other words, the coccidiosis-relieving agent of the present invention follows with the tendency of the art toward the reduction of damage to poultry by relieving lesions while allowing the growth of Coccidium protozoa and imparting sufficient immunological stimuli. Moreover, since the active components of the coccidiosis-relieving agent of the present invention are extracted from a naturally occurring substance, it is expected that the agent of the present invention can be used one week before shipping of broilers, though the administration of the existing drugs is prohibited at that time.

To further illustrate the present invention in greater detail, and not by way of limitation, the following Examples will be given.

EXAMPLE 1

Male broilers aged 7 days were divided into 8 groups each having 10 birds and allowed to take feeds differing in the content of anacardic acids (0, 0.1, 0.4 or 0.8% by weight) ad libitum. On the age of 10 days, $2 \times 10^3$ or $5 \times 10^4$ oocysts of E. tenella were administered to the birds. On the age of 17 days, the cecal length, the lesion index and the cecal oocyst count were examined. At the same time, the body weight gain, the liver weight and the abdominal fat amount were also measured. Table 1 shows the results in which each value represents the average of the group.

TABLE 1

Effect of ad lib. intake of anacardic acids-containing feed

| Oocyst infection anacardic acid | 0 | $2 \times 10^3$ | | | $5 \times 10^4$ | | | |
|---|---|---|---|---|---|---|---|---|
| content (wt. %) | 0 | 0 | 0.4 | 0.8 | 0 | 0.1 | 0.4 | 0.8 |
| body weight gain (g) | 345 | 344 | 325 | 302** | 303 | 331 | 319 | 299 |
| cecal length (cm, total) | 20.2 | 19.0 | 18.9 | 18.6 | 12.3 | 13.0 | 13.2 | 14.3 |
| lesion index | 0 | 1.1 | 1.1 | 0.5 | 3.4 | 3.0 | 2.5* | 2.6 |
| cecal oocyst count (log OPC) | 0 | 6.54 | 6.53 | 6.76 | 7.29 | 7.03 | 7.41 | 7.40 |
| liver weight (g) | 12.9 | 13.3 | 13.1 | 12.5 | 13.8 | 16.6** | 14.0 | 14.6 |
| abdominal fat | 4.1 | 5.2 | 4.5 | 3.9** | 4.1 | 4.0 | 4.5 | 3.4 |

*A significant difference (P < 0.05) from the data of the control group (no anacardic acid) of the same infection level.
**A significant difference (P < 0.01) from the data of the control group (no anacardic acid) of the same infection level.

EXAMPLE 2

Male broilers aged 7 days were divided into 9 groups each having 10 birds and allowed to take feeds differing in the content of cashew nut shell oil (0, 0.1, 0.2 or 0.4% by weight) ad libitum. On the age of 10 days, $1\times10^4$ or $1\times10^5$ oocysts of *E. tenella* were administered to the birds. On the age of 17 days, the cecal length, the lesion index and the cecal oocyst count were examined. At the same time, the body weight gain was also measured. Table 2 shows the results in which each value represents the average of the group.

TABLE 2

| Oocyst infection cashew nut shell | Effect of ad lib. intake of cashew nut shell oil-containing feed | | | | | | | | |
|---|---|---|---|---|---|---|---|---|---|
| | 0 | $1\times10^4$ | | | | $1\times10^5$ | | | |
| oil content (wt. %) | 0 | 0 | 0.1 | 0.2 | 0.4 | 0 | 0.1 | 0.2 | 0.4 |
| body weight gain (g) | 240 | 239 | 263 | 293* | 259 | 279 | 294 | 258 | 282 |
| cecal length (mm, average) | 89.1 | 95.2 | 81.9* | 94.2 | 101.7 | 92.3 | 87.2 | 91.0 | 98.1 |
| lesion index | 0 | 1.8 | 2.7 | 0.5* | 0.2** | 2.5 | 2.3 | 2.3 | 1.3* |
| cecal oocyst content (log OPC) | 0 | 6.71 | 6.35 | 6.49 | 5.91 | 7.17 | 7.02 | 7.13 | 7.11 |

*A significant difference (P < 0.05) from the data of the control group (no cashew nut shell oil) of the same infection level.
**a significant difference (P < 0.01) from the data of the control group (no cashew nut shell oil) of the same infection level.

EXAMPLE 3

To examine the effect of anacardic acids, the procedure of Example 1 was repeated but using white leghorns as the substitute for the broilers. On the age, of 10 days, $2\times10^3$ oocysts of *E. tenella* were administered to the birds. On the age of 17 days, the cecal length, the lesion index, the cecal oocyst count and the body weight gain were examined. The results thus obtained showed almost the same tendencies as those of the data given in Table 1 of Example 1.

In the above Examples 1 and 3, the administration of anacardic acids (AA) decreased the coccidiosis lesion index compared with the control group to which no anacardic acids was added. This tendency became more remarkable with an increase in the administration level of the oocysts.

In Example 2, the administration of 0.4% of cashew nut shell oil (CO) slightly relieved cecal contraction. Significant decrease in coccidiosis lesion index were observed in the 0.2% and 0.4% CO-administered group when $1\times10^4$ oocysts were inoculated and the 0.4% CO-administered group when $1\times10^5$ oocysts were inoculated.

These facts prove that the administration of AA or CO relieved lesions. Regarding cecal oocyst count, however, the administration of AA or CO achieved scarcely any effect. On the other hand, bodyweight gain decreased with an increase in the amount of AA administered in the $2\times10^3$ and $5\times10^{10}$ oocyst-inoculated group (Example 1). The 0.8% AA-administered group showed a definite decrease in body weight gain. In other groups, the addition of AA or CO caused no large change. These results clearly indicate that AA and CO relieve lesions, though they do not suppress the growth of Coccidium protozoa.

While the invention has been described in detail and with reference to specific examples thereof, it will be apparent to one skilled in the art that various changes and modifications can be made therein without departing from the spirit and scope thereof.

What is claimed is:

1. A method of relieving coccidiosis in animals which comprises adding at least one member selected from the group consisting of cashew nut shell oil and anacardic acids to a feed in an amount effective to relieve coccidiosis and giving animals the resulting feed.

2. The method as claimed in claim 1, wherein said at least one member selected from the group consisting of cashew nut shell oil and anacardic acids is added to the feed in an amount of 0.01 to 5% by weight.

3. The method as claimed in claim 2, wherein said animals are poultry.

4. The method as claimed in claim 1, wherein said animals are avians and said coccidiosis is arian coccidiosis.

5. The method as claimed in claim 1, wherein said at least one member selected from the group consisting of cashew nut shell oil and anacardic acids is added to the feed in an amount of from 0.1 to 1.0% by weight.

6. The method as claimed in claim 1, wherein said at least one member selected from the group consisting of cashew nut shell oil and anacardic acids is added to the feed in an amount 0.1 to 0.8% by weight.

7. A method of relieving coccidiosis in animals which comprises determining an amount of a member selected from the group consisting of cashew nut oil and anacardic acids effective to relieve coccidiosis and adding said at least one member in an amount effective to relieve coccidiosis to a feed and giving animals the resulting feed.

8. The method as claimed in claim 7, wherein said at least one member selected from the group consisting of cashew nut shell oil and anacardic acids is added to the feed in an amount of 0.01 to 5% by weight.

9. The method as claimed in claim 7, wherein said animals are poultry.

10. The method as claimed in claim 12, wherein said animals are avians and said coccidiosis is avian coccidiosis.

11. The method as claimed in claim 7, wherein said at least one member selected from the group consisting of cashew nut shell oil and anacardic acids is added to the feed in an amount of from 0.1 to 1.0% by weight.

12. The method as claimed in claim 7, wherein said at least one member selected from the group consisting of cashew nut shell oil and anacardic acids is added to the feed in an amount 0.1 to 0.8% by weight.

* * * * *